Figure 1:
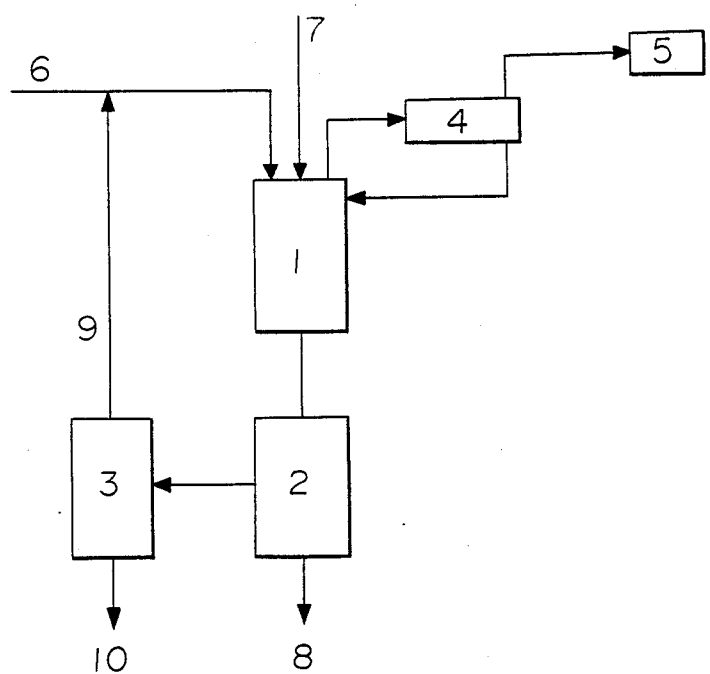

United States Patent [19]

Tan et al.

[11] Patent Number: 4,900,821

[45] Date of Patent: Feb. 13, 1990

[54] METHOD FOR PRODUCING HIGH-PURITY CAPROLACTAM

[75] Inventors: Kazuo Tan; Takashi Hironaka; Michio Nakamura, all of Kitakyushu, Japan

[73] Assignee: Mitsubishi Kasei Corporation, Tokyo, Japan

[21] Appl. No.: 330,695

[22] Filed: Mar. 30, 1989

[30] Foreign Application Priority Data

Apr. 9, 1988 [JP]  Japan ................................. 63-87947

[51] Int. Cl.$^4$ .......................................... C07D 201/16
[52] U.S. Cl. .................................................. 540/540
[58] Field of Search ......................................... 540/540

[56] References Cited

U.S. PATENT DOCUMENTS 2,813,858 11/1987 Joris .................................... 540/540
3,426,744 11/1969 Berther et al. ..................... 540/540

*Primary Examiner*—Robert T. Bond
*Attorney, Agent, or Firm*—Oblon, Spivak, McClelland, Maier & Neustadt

[57] ABSTRACT

A method for producing high-purity caprolactam from a mixture comprising a melt of crude caprolactam and water, which comprises cooling the mixture in a crystallizer under a reduced pressure of from 1 to 22 Torr while maintaining the water concentration in the mixture at a level of from 0.5 to 10% by weight, to crystallize high-purity caprolactam, and then separating the resulting crystals.

4 Claims, 1 Drawing Sheet

METHOD FOR PRODUCING HIGH-PURITY CAPROLACTAM

The present invention relates to a method for producing high-purity caprolactam. More particularly, it relates to a method for producing high-purity caprolactam by letting high-purity caprolactam crystallize from molte caprolactam under a certain specific condition, followed by separation of the resulting crystals.

Caprolactam is useful as starting material for fibers or shaped products of a polyamide resin. In order to obtain a final product of good quality, the caprolactam is required to be highly pure. Many methods have been known for the purification of caprolactam. As one of such purification methods, crystallization may be mentioned, and as a solvent useful for crystallization, an organic solvent, for example, an aromatic hydrocarbon such as benzene or toluene, an aliphatic hydrocarbon such as hexane, heptane or cyclohexane, an alcohol such as propanol or butanol, or a chlorinated hydrocarbon such as perchloroethylene, or water, has been known (See e.g. Japanese Examined Patent Publication No. 5920/1964 and Japanese Unexamined Patent Publication No. 54095/1973.) However, in the caprolactam crystallized by means of such an organic solvent, the organic solvent remains as one of impurities, and an additional purification is required to remove this organic solvent. Usually, caprolactam obtained in such a manner, is subjected to purification by distillation. On the other hand, when crystallization is conducted by using water as the solvent, precipitated crystals have a high water content and can not be used as high-purity caprolactam. Thus, the purification method based on crystallization by means of a solvent, is industrially disadvantageous since, for example, it requires a step of removing the solvent from crystals.

A method is conceivable wherein caprolactam is brought to a molten state substantially in the absence of a solvent and then cooled for crystallization. However, if a melt of caprolactam is crystallized in the absence of a solvent in a crystallizer of external cooling system, crystals precipitating on the wall surface tend to be very fine, and they tend to be firmly fixed to the wall surface, so that the scraping operation and the subsequent separation operation will be difficult. Namely, such a method has a drawback such that a continuous operation on an industrial scale is difficult.

The present inventors have conducted extensive studies to overcome such drawbacks of the conventional methods and as a result, have found it possible to precipitate readily separable crystals having a large particle size without requiring any scraping operation of firmly fixed crystals, by a method wherein a certain specific amount of water is added to molten caprolactam to prepare a mixture, and the mixture is introduced into a crystallizer and cooled under reduced pressure at a certain specific level of pressure by means of latent heat of evaporation of caprolactam and water. Further, according to this method, the water content in the crystals can directly be controlled to an acceptable range to obtain high-purity caprolactam, as is different from the usual crystallization by means of solvent.

The present invention provides a method for producing high-purity caprolactam from a mixture comprising a melt of crude caprolactam and water, which comprises cooling the mixture in a crystallizer under a reduced pressure of from 1 to 22 Torr while maintaining the water concentration in the mixture at a level of from 0.5 to 10% by weight, to crystallize high-purity caprolactam, and then separating the resulting crystals.

In the accompanying drawing, FIG. 1 illustrates an embodiment of an apparatus to carry out the present invention.

Now, the present invention will be described in detail with reference to the preferred embodiments.

The crude caprolactam to be treated by the present invention may usually be crude caprolactam obtained by subjecting cyclohexanone oxime to rearrangement in a sulfuric acid medium, then neutralizing the medium with e.g. aqueous ammonia, extracting caprolactom from the resulting aqueous solution of the inorganic salt with a solvent having a high dissolving power, such as benzene, followed by distillation of the solvent. Further, it may be crude caprolactam obtained as an initial fraction or a last fraction recovered by fractional distillation of such crude caprolactam. Such crude caprolactam usually contains a few percents of impurities such as aminocaproic acid or aniline.

In the purification by crystallization of such crude caprolactam according to the present invention, a mixture of crude caprolactam in a molten state and water, is formed, and this mixture is subjected to cooling under reduced pressure to crystallize caprolactam. This cooling under reduced pressure means cooling by means of latent heat of evaporation when water and caprolactam in the mixture are evaporated under reduced pressure. Namely, it is a significant feature of the present invention that the cooling surface is not the wall surface of the crystallizer, but is the liquid surface constituting the mixture. The water concentration in the mixture is maintained at a level of from 0.5 to 10% by weight, preferably from 1 to 8% by weight. If the water concentration is too low, a high level of pressure reduction is required to cool the mixture of the molten caprolactam and water to the crystallization temperature by the latent heat of evaporation, such being undesirable. On the other hand, if the water concentration is too high, the crystallization temperature tends to be too low, and the water content in recovered caprolactam crystals tends to be high, such being undesirable. Water may be supplied directly to the crystallizer or may be mixed with caprolactam prior to the supply to the crystallizer. The pressure in the crystallizer is from 1 to 22 Torr, preferably, from 5 to 20 Torr. If the pressure is too low, such is industrially disadvantageous. On the other hand, if the pressure is too high, the cooling effect will be small, whereby crystallization will be difficult.

Here, the temperature for crystallization at the water concentration of the present invention is usually from 30° to 65° C.

In carrying out the crystallization method of the present invention, for example, by a continuous method, firstly, a melt of crude caprolactam is charged through a line 6 into a crystallizer 1, and the melt is continuously supplied from the line 6. On the other hand, water is supplied from a line 7, so that the concentration of water in the mixture comprising the melt of crude caprolactam and water is adjusted to a level of from 0.5 to 9% by weight. The pressure in the crystallizer 1 is adjusted by an ejector 5 to a level of from 1 to 22 Torr to cool the mixture under reduced pressure. Water evaporated from the crystallizer 1 is condensed by a condenser 4. Condensed water contains a small amount of caprolactam, and such water is usually recycled to the crystallizer 1 and used to control the water concentration.

A slurry containing caprolactam crystallized in the crystallizer 1 is supplied to a solid-liquid separator 2, whereby caprolactam crystals are recovered from a line 8.

The separation of caprolactam crystals in the crystalizer 1 can be conducted by a separator such as a centrifuge, a cyclone (solid-liquid) or a decanter. In such a case, the separated crystals are in the form of a paste having some content of liquid caprolactam or a highly concentrated slurry. The smaller the liquid caprolactam content, the better the purification effects. If necessary, the obtained crystals may further be purified by another purification process such as a column type melt purification or distillation method.

On the other hand, the melt of crude caprolactam as the separated mother liquid is collected to a mother liquid tank 3 and recycled to the crystallization step through a line 9, although a part thereof is withdrawn for another purification step.

Now, the present invention will be described in further detail with reference to Examples. However, it should be understood that the present invention is by no means restricted by such specific Examples. The permanganate value (Pz) and the permanganate consumption (PM) in the Examples were measured in accordance with the following methods.

PZ (permanganat-zahl: permanganate number)

1 g of a sample of caprolactam was dissolved in 100 ml of water, and 1 ml of a 0.01N potassium permanganate aqueous solution was added thereto. After 60 minutes, the transmittance of a light having a wavelength of 410 nm was measured and represented by the unit of percent.

PM (permanoanat-menge: permanganate consumction)

100 g of a sample of caprolactam was dissolved in 150 ml of 8M sulfuric acid, and the solution thereby obtained was titrated with a 0.1N potassium permanganate aqueous solution, whereby the consumption of potassium permanganate was measured and represented by the unit of ml/kg-caprolactam.

EXAMPLE 1

Into a 40 l crystallizer of an agitation tank type equipped with a condenser at the top, 20 l of molten crude caprolactam (Pz 32, PM 20 ml/kg) was charged as the base material, and water was added to bring the water concentration to 2% by weight. The pressure in the crystallizer was adjusted to 15 Torr by the ejector, and the temperature for crystallization was adjusted to about 60° C. To this system, 5 kg/hr of the above-mentioned melt of crude caprolactam and water in an amount to bring the water content in the mixture to a level of 2% by weight, were continuously supplied for crystallization. On the other hand, a slurry containing precipitated crystals was withdrawn at a rate of 20 kg/hr. The withdrawn slurry was subjected to centrifugal separation to recover purified caprolactam crystals at a rate of about 4 kg/hr. On the other hand, the separated mother liquor was purged at a rate of 1 kg/hr, and the rest was recycled to the crystallizer for reuse. The potassium permanganate values (PZ, PM), the water content and the perticle size of the crystals thus obtained, were measured. The results are shown in Table 1.

EXAMPLE 2

The operation was conducted in the same manner as in Example 1 except that the water concentration in the mother liquor in the crystallizer was adjusted to 8% by weight, and the mixture was cooled to about 47° C under a pressure of 15 Torr. The yield of the crystals obtained by crystallization and separation was about 80% based on the supplied caprolactam. The results of the evaluation are shown in Table 1.

EXAMPLE 3

The operation was conducted in the same manner as in Example 1 except that the water concentration was adjusted to 2% by weight, and the mixture cooled to about 60° C. under a pressure of 10 Torr. The yield of the crystals obtained by crystallization and separation was about 80% based on the supplied caprolactam. The results of the evaluation are shown in Table 1.

COMPARATIVE EXAMPLE 1

The operation was conducted in the same manner as in Example 1 except that the water concentration was adjusted to 2% by weight, and the mixture was cooled under a pressure of 25 Torr. However, it was thereby impossible to cool the mixture to the crystallizing temperature, and no crystallization was carried out.

COMPARATIVE EXAMPLE 2

The operating was conducted in the same manner as in Example 1 except that the water concentration was adjusted to 15% by weight, and the mixture was cooled to about 22° C under a pressure of 10 Torr. The yield of the crystals obtained by crystallization and separation was about 80%, based on the supplied caprolactam. The results of evaluation are shown in Table 1.

REFERENCE EXAMPLE

By using a 40 l crystallizer of an external cooling and scraping system, crystallization was conducted at about 60° C with the same starting materials as in Example 1 at a water concentration of 2% whereby caprolactam formed on the inner wall of the crystallizer was so firmly fixed that it was impossible to scrape it, and the operation had to be terminated in about 6 hours. The crystals obtained by the termination were fine crystals, and the quality was at such a level that PM was 5 ml/kg and Pz was 79%. The results of the evaluation are shown in Table 1.

TABLE 1

| | | Example 1 | Example 2 | Example 3 | Comparitive Example 1 | Comparitive Example 2 | Reference Example |
|---|---|---|---|---|---|---|---|
| Starting material | Pm (ml/kg) | 20 | 20 | 20 | 20 | 20 | 20 |
| | Pz (%) | 32 | 32 | 32 | 32 | 32 | 32 |
| Conditions for crystallization | Pressure(Torr) | 15 | 15 | 10 | 25 | 10 | 760 |
| | Temp. (°C.) | 60 | 47 | 60 | — | 23 | 60 |
| | Water (%) concentration | 2 | 8 | 2 | 2 | 15 | 2 |
| | Pm (ml/kg) | 4 | 5 | 4 | — | 6 | 5 |

TABLE 1-continued

|  |  | Example 1 | Example 2 | Example 3 | Comparitive Example 1 | Comparitive Example 2 | Reference Example |
|---|---|---|---|---|---|---|---|
| Quality of crystals | Pz (%) | 82 | 83 | 81 | — | 77 | 79 |
|  | $H_2O$ (ppm) | 180 | 920 | 210 | — | 2100 | 280 |
|  | $D_{50}$* ($\mu$) | 810 | 500 | 720 | — | 290 | 200 |
|  |  |  |  |  | Not crystallized |  | Operation terminated in 6 hours |

*$D_{50}$ indicates an average particle size of crystals.

According to the present invention, it is possible to recover crystals of purified caprolactam from the melt of crude caprolactam without using any special solvent, whereby no step for the removal of a solvent from crystals is required. Further, according to the present invention, the resulting caprolactam crystals are large in size, whereby not only the filtability is excellent, but the purification degree is very high. Furthermore, by the crystallization of the present invention, it is possible to obtain crystals having a very small water content, whereby a product can readily be recovered simply by solid-liquid separation of the mother liquid slurry without requiring a step of e.g. drying.

We claim:

1. A method for producing high-purity caprolactam from a mixture comprising a melt of crude caprolactam and water, which comprises cooling the mixture in a crystallizer under a reduced pressure of from 1 to 22 Torr while maintaining the water concentration in the mixture at a level of from 0.5 to 10% by weight, to crystallize high-purity caprolactam, and then separating the resulting crystals.

2. The method according to claim 1, wherein the water concentration in the mixture is maintained at a level of from 1 to 8% by weight.

3. The method according to claim 1, wherein the reduced pressure is at a level of from 5 to 20 Torr.

4. The method according to claim 1, wherein the temperature for crystallization is within a range of from 30° to 65° C.

* * * * *